US 9,737,560 B1
Aug. 22, 2017

(12) United States Patent
Shulgin et al.

(54) PROCESS FOR PREPARATION OF A HUMIC SUBSTANCE BASED GEL FOR TARGETED EXTERNAL APPLICATION

(71) Applicant: BlackBalm, LLC, Louisville, KY (US)

(72) Inventors: Alexander I. Shulgin, Louisville, KY (US); Jeffrey L. Sangalli, Louisville, KY (US)

(73) Assignee: BlackBalm, LLC, Louisville, KY (US)

( * ) Notice: Subject to any disclaimer, the term of this patent is extended or adjusted under 35 U.S.C. 154(b) by 139 days.

(21) Appl. No.: 14/669,347

(22) Filed: Mar. 26, 2015

Related U.S. Application Data

(60) Provisional application No. 62/049,665, filed on Sep. 12, 2014.

(51) Int. Cl.
| | |
|---|---|
| *A61K 31/765* | (2006.01) |
| *A61K 9/00* | (2006.01) |
| *A61K 31/60* | (2006.01) |
| *A61K 47/12* | (2006.01) |
| *A61K 47/10* | (2017.01) |
| *A61K 47/02* | (2006.01) |
| *B65D 25/20* | (2006.01) |
| *B65D 85/00* | (2006.01) |

(52) U.S. Cl.
CPC .......... *A61K 31/765* (2013.01); *A61K 9/0014* (2013.01); *A61K 31/60* (2013.01); *A61K 47/02* (2013.01); *A61K 47/10* (2013.01); *A61K 47/12* (2013.01); *B65D 25/205* (2013.01); *B65D 85/70* (2013.01)

(58) Field of Classification Search
CPC .... A61K 31/765; A61K 9/0014; A61K 31/60; A61K 47/02; A61K 47/10; A61K 47/12; B65D 25/205; B65D 85/70
See application file for complete search history.

(56) References Cited

U.S. PATENT DOCUMENTS 3,398,186 A * 8/1968 Schwartz ................ C05F 11/02
562/405
5,276,032 A * 1/1994 King .................... A61K 9/0014
514/238.2

* cited by examiner

*Primary Examiner* — Alma Pipic
(74) *Attorney, Agent, or Firm* — Middleton Reutlinger

(57) ABSTRACT

A method of production and composition of a humic substances-based topical gel that contains a high concentration of polymerized humic substances in the form of polyelectrolyte-enhanced biopolymers, allowing for targeted application of gel to skin. A method of production consists of selection of humic substances containing material, extraction of humic substances from the material, polymerization of humic substances, and further processing for product preservation. Such humic substances based material may be derived from brown coal, such as leonardite or lignite, or peat. An extraction technique for extraction of the humic substances is an alkali extraction method. Such a resulting composition may contain sodium silicate as a gelling agent for ease of application, and in some embodiments a preservative or combination of preservatives for shelf life. Such a humic substances-based topic gel is water soluble, allowing for in-home application and ability to discard through washing down a household drain.

17 Claims, No Drawings

PROCESS FOR PREPARATION OF A HUMIC SUBSTANCE BASED GEL FOR TARGETED EXTERNAL APPLICATION

CROSS-REFERENCE TO RELATED APPLICATIONS

Priority is claimed on the basis of U.S. Provisional Application No. 62/049,665, filed on 12 Sep. 2014.

FIELD OF THE INVENTION

A process such as is described in various embodiments herein generally relates to manufacturing of a humic substances-based topical gel for targeted external use. A manufacturing process for a humic substances-based topical gel may comprise selection of humic substances containing material, extraction of humic substances from the material, polymerization of humic substances, and further processing for product preservation. An embodiment is directed to use of brown coal, such as leonardite or lignite, or peat, as a selected humic substances containing material. An embodiment is directed to use of an alkali extraction method for extraction of humic substances. An embodiment may comprise a method of preserving a product.

A composition of humic substances-based topical gel such as is described herein may contain a high concentration of polymerized humic substances in a form of polyelectrolyte-enhanced biopolymers, allowing for targeted application. Such a composition may comprise sodium silicate as a gelling agent for ease of application, and in some embodiments a preservative or combination of preservatives for shelf life. A humic substance-based topical gel may be used in treatment of musculoskeletal disorders such as varied forms of arthritis, including rheumatoid arthritis, polyarthritis, and other types of inflectional arthritis (except tuberculosis arthritis); osteitis; periostitis; diseases of nervous system, including intoxication of central and peripheral nervous system, paralysis, spinal radiculitis; polyneuropathy; diseases of digestive system such as chronic gastritis, perioduodenal and other types colitis, proctitis (with the exception of sharp stages), chronic hepatitis, chronic cholecystitis; gynecological disorders such as infertility or hormone deficiency, uterus post-inflammation syndrome; male-system disorders such as chronic prostatitis, epididymitis, etc.; uretic system disorders such as pielocystitis, cystitis, urethritis, etc.; and, other conditions such as chronic sinusitis, tonsillitis, etc. and many skin diseases. Such a gel composition may also have anti-inflammatory and anti-allergic properties. Use of a humic substances-based topical gel produced by the described method may also be by individuals, for example athletes, to aid in targeted muscle relief and recovery. Such a gel may be used alone or in combination with other physical therapy methods such as electrophoresis, ultrasound, sonophoresis and ionophoresis. A humic substances-based topic gel is water soluble and therefore can be applied to a target area by a user in their home, training facility, etc. and then discarded by washing down a household drain.

BACKGROUND OF THE INVENTION

Therapeutic muds have long been used to promote physical recovery and healing. These therapeutic muds are comprised of decomposed and humificated organic matter, bacteria, enzymes, amino acids, various types of clay, minerals, salts, and gases. Therapeutic muds, due to the nature of being harvested from the ground, often lack consistency in composition and properties from location to location. Chemical analyses have revealed that specific stable organic compounds, known as humic substances with primarily humic acids, are present in therapeutic muds and drive their biological and therapeutic action.

Humic substances, including primarily humic and fulvic acids and humin, have been shown to have a number of beneficial properties, including: stimulating the immune system; acting as an antibacterial, antiviral, and antifungal agent; and acting as an anti-inflammatory. Furthermore, humic substances are common in the biosphere: soil, natural water, bottom sediment, etc. being the largest reservoir of organic carbon in nature. In particular, humic substances in the soil contribute to soil native properties and functions as well as fertility through stimulating microbial organisms and stabilizing nutrients in the soil. Humic substances in their native state do not have significant biological and chemical activity, because their main active functional groups are blocked by metal cations, primarily calcium, magnesium, fine clay minerals and structural coagulation.

While therapeutic muds have been used by people for centuries, they have a number of limitations. These muds, because they are harvested from the ground, are subject to contamination and the effects of pollution, in addition to being inconsistent from location to location. Furthermore, therapeutic muds require as many as 15 full body applications, applied by a professional, in order to be effective, making them both costly and time consuming. Lastly, therapeutic muds are not easily discarded, and often require a mud bath to remove.

The art discloses humic or fulvic acid based products for dietary or nutritional supplementation, promotion of hair growth and heath, and amelioration of certain skin conditions (e.g. acne, athlete's foot, eczema, etc.) and promotion of skin health. However, there exists a need in the art for a concentrated and active humic acids-based product for external application that is applicable by a user to a targeted area of the body (for healing of diseases or for relief of muscle soreness) in the privacy of their home, training facility, etc. that can be simply discarded by washing down the drain.

SUMMARY

The present disclosure is directed towards a method of production and composition of a humic substances based gel for targeted external application. A method of production for such a humic substances-based gel may comprise extracting humic substances, primarily humic and fulvic acids, from brown coal and/or peat using an alkaline extraction process; wherein, the humic substances may contain, for example, at least about 20% humic acid, less than about 30% ash, a moisture content from about 10% to about 17%, and a concentration of heavy metals and benzyprene no greater than that of environmental soils. Extraction of humic acids results in their active functional groups freeing from metal cations and fine clay minerals, and conversion to negatively charged completely opened up volumetric molecules. A liquid product of such an extraction may be subjected to a polymerizing step and/or a preserving step which may make the resulting product even better suited for cosmetic or pharmaceutical use. In some embodiments brown coal, such as leonardite or lignite, is a starting material.

An alkaline extraction may comprise agitated stirring of a mixture containing water, for example, distilled water (for example, about 82%), heated to, for example, from about 75° C. to about 85° C., brown coal (for example, about 16%), potassium hydroxide (for example, about 2.7%), or sodium hydroxide (for example, about 1.7%), or a mixture of the two, such as potassium hydroxide (such as about 2.2%) and sodium hydroxide (such as about 0.3%), for about 15 minutes. An alkaline extraction may further comprise stabilization of such a mixture, which is controlled by the pH of such mixture reaching a constant value for about 24 hours, and precipitation of solids, wherein remaining solids are precipitated from a supernatant liquid. Such remaining liquid may be filtered, for example, through a 75 μm or smaller filter.

In some embodiments, agitated stirring may be conducted in an industrial mixer or blender at about 1000 rpm initially, in order to engage all brown coal in treatment and avoid precipitation. Mixing speed may be reduced, for example, to about 700 rpm to reduce particulates, excessive grinding, and fine stable suspension formation.

In some embodiments, a process for stabilizing such a mixture may comprise allowing an initial mixture pH of from about 9 to about 9.5 to increase to a pH of from about 9.5 to about 10.5. Precipitating solid from supernatant may comprise allowing such a mixture to sit undisturbed for about 24 hours such that solid will settle, for example, at the bottom of a container or mixer or blender.

In some embodiments, a process of precipitating solid from supernatant may comprise use of a centrifuge such that solid particulates form a pellet.

A polymerizing step may comprise heating supernatant to from about 72° C. to about 80° C., adding sodium silicate solution at from about 0.3% to about 0.5% dry weight, adding about 0.08% sodium carbonate, adding from about 4 to about 8 drops of sulfuric acid and then adding hydrochloric acid solution to reach a pH between about 7.0 and about 7.4, such as 7.2. During mechanical stirring of such a mixture, temperature may be slowly reduced to from about 45° C. to about 50° C. for from about 30 to about 35 minutes, until such mixture has a gelatinous consistency at a temperature from about 45° C. to about 50° C. Periodic foam removal may be undertaken.

In some embodiments, a preserving step may comprise adding a commercially available preservative package suitable for cosmetic or pharmaceutical use. In some embodiments, such a commercially available preservative package may be Geogard™ ETC.

In some embodiments, a preserving step may comprise pasteurizing such a liquid mixture.

A topical gel composition for targeted application to skin may comprise about 98.5% polyelectrolyte-enhanced biopolymer extracted using an alkaline extraction method from brown coal and/or peat and polymerized with addition of sodium carbonate, sulfuric acid and hydrochloric acid; from about 0.3% to about 0.5% of sodium silicate dry weight, which functions as a solidifying agent and gives a resultant product a gelatinous consistency; from about 0.38% to about 0.42% benzyl alcohol; from about 0.04% to about 0.07% salicylic acid; from about 0.015% to about 0.025% glycerin; and from about 0.005% to about 0.02% sorbic acid. A polyelectrolyte-enhanced biopolymer of such a disclosed composition comprises concentrated polymerized humic substances extracted from, for example, leonardite or lignite and converted into polyelectrolyte enhanced biopolymer with sodium carbonate, sulfuric acid and hydrochloric acid additives. In such a composition, benzyl alcohol, salicylic acid, glycerin, and sorbic acid may constitute components of a commercially available preservative package suitable for cosmetic or pharmaceutical use.

In some embodiments, a composition such as is disclosed herein may be used for healing of diseases and/or relief of sore muscles, tendons and ligaments.

It should be appreciated that all combinations of the foregoing concepts and additional concepts discussed in greater detail below provided such concepts are not mutually inconsistent are contemplated as being part of the subject matter disclosed herein. In particular, all combinations of claimed subject matter appearing at the end of this disclosure are contemplated as being part of the subject matter disclosed herein.

DETAILED DESCRIPTION

A process such as is described in various embodiments herein now will be described more fully hereinafter. A process such as is described in various embodiments herein may, however, be embodied in many different forms and should not be construed as limited to the embodiments set forth herein; rather, these embodiments are provided so that this disclosure will be thorough and complete, and will fully convey the scope of a process such as is described in various embodiments herein to those skilled in the art. Also, it is to be understood that the phraseology and terminology used herein is for the purpose of description and should not be regarded as limiting. When used in this description and the claims as an adverb rather than a preposition, "about" means "approximately" and comprises the stated value and every value within 10% of that value; in other words, "about 100%" includes 90% and 110% and every value in between.

A quantity of humic substance containing granular material is selected, and from said selected material humic substances are extracted. Selection of the granular humic substance containing material may vary; preferably brown coal, such as leonardite or lignite, may be obtained for extraction and processing. Humic acid content of selected brown coal may be, for example, about 20% or higher, and its ash content may be, for example, about 30% or less, such that humic acid is readily available for extraction, and separation from inert compounds, i.e. ash forming minerals, and activation through a process such as is described herein. Furthermore, such a selected brown coal may, for example, have a moisture content of from about 10% to 17%, meaning some naturally hydrated humic substances may be present. Such a selected brown coal may not have a concentration of heavy metals and benzyprene that exceeds a concentration of typical environmental soils, for example agricultural soils, which ensures elimination of excessive heavy metals and benzyprene from final product, such that their concentration is below their trace level in the environment. Excessive heavy metals, for example lead or mercury, can be absorbed through the skin and cause heavy metal toxicity; while, benzyprene is a polycyclic aromatic hydrocarbon with mutagenic and carcinogenic properties.

According to a process such as is described herein, a selected granular brown coal undergoes an extraction process wherein humic substances, stable organic compounds being irregular biopolymers, such as humic and fulvic acids, are extracted, and humin is suspended to some degree. An extraction process may begin with heating a mixture of granular brown coal and water, or by heating water alone. If a mixture, such a mixture may have about 82% total weight water and be heated to a temperature of from about 75° C. to about 85° C. A temperature below about 75° C. may lead to less efficacy of humic substances extraction, and a temperature above 85° C. may result in water evaporation from the surface. Distilled or deionized water may be used. Once such a mixture, or water, is thoroughly heated, about 2.7% total weight potassium hydroxide, or about 1.7% total weight sodium hydroxide, or a mixture of the two, may be added to such a mixture. For example, potassium hydroxide about 2.2% and sodium hydroxide about 0.3% may be added to such a mixture. Potassium hydroxide and/or sodium hydroxide may be added in a form of dry, solid, pellets or flakes rather than being previously dissolved in solvent. Interaction of dry potassium hydroxide and/or sodium hydroxide interaction with water in such a mixture is exothermic and may result in a rapid increase in temperature of such a mixture. Such a temperature increase may be in a range of, for example, from about 3° C. to about 5° C. After such a temperature increase, temperature of such a mixture, or water, may return back to a temperature of from about 75° C. to about 85° C. during a next stage of such a process. An alkali, or an alkali mix, suitable for addition to such a mixture may have a pH of from about 11 to about 12. Following addition of alkali, and a consequent temperature increase, an amount of a selected granular brown coal may be added, which may result in temperature reduction to attain a temperature of from about 75° C. to about 85° C. Such a resultant alkaline brown coal liquid mixture may be stirred in an industrial mixer or blender at about 1000 rpm initially to engage all brown coal in treatment and avoid its precipitation. Such stirring may be then slowed to about 700 rpm to reduce excessive coal granules, grinding, and fine suspension formation. Temperature may be maintained within a range of from about 75° C. to about 85° C. Such a temperature range may also allow for inactivation of many human commensal and pathogenic bacteria, or, in other words, may effect pasteurization.

Such stirring may last for about 15 minutes. Shorter stirring times may result in less efficacy of humic substances extracted, while longer stirring times may result in excessive coal granules grinding and stable fine suspension formation, making separating liquid phase from solid phase difficult and time-consuming. Such mechanical stirring allows such brown coal to break up into smaller pieces, but not fines, increasing surface area for reaction with water and bases to occur. An alkali liquid solution reacts with brown coal, and humic substances are extracted from such brown coal. Stirring and temperature conditions such as are described herein contribute to intensification and optimization of such an extraction process. After, for example, from about 5 to about 7 minutes of stirring and agitating, if foam is present in the mixture, this foam may be then skimmed from the top of the mixture. Alkali media, temperature, and intensive stirring may allow the mixture to undergo pasteurization. After about 15 minutes of, for example, constant stirring and agitating, a remaining brown-black liquid may contain a high concentration of active humic substances at a pH range of from about 9 to about 10. Trace amount of metals may turn into insoluble metal hydroxides which may precipitate together with brown coal precipitants.

As an illustrative example, for a process in which about 577 grams of leonardite was to be subjected to extraction, an amount of about 3000 grams of distilled water was heated. Once such water was thoroughly heated to a temperature of from about 75° C. to about 85° C., about 83 grams of potassium hydroxide and about 11 grams of sodium hydroxide were added. A quantity of 577 g of granular leonardite was added to such a mixture of heated water and alkali, and the resultant mixture further treated according to a process such as is described herein.

In some embodiments, a process of mixture stabilization may comprise allowing an initial mixture pH of from about 9 to about 10 to increase to, for example, a pH of from about 9.5 to about 10.5. Remaining solids, including metal hydroxide precipitates, may be separated from supernatant liquid of such a mixture. In some embodiments, such separation may be effected by allowing the mixture to sit undisturbed for a period of time, such as 24 hours. During that time solid particles may settle to the bottom, allowing supernatant liquid to be removed from the top of the separated mixture and retained for further processing. In other embodiments, precipitation may be effected through use of a centrifuge, wherein gravitational and/or centrifugal force of centrifugation may push solid particles to form a pellet at the bottom and/or periphery of a tube, allowing supernatant liquid to be removed from the top and retained for further processing. Following precipitation, precipitated solid may be discarded, and supernatant liquid may be filtered through, for example, a 75 μm or smaller filter to remove remaining small solid particles. Remaining supernatant liquid may have a pH of, for example, from about 9.5 to about 10.5.

In preparation for a polymerizing process, such supernatant liquid may be heated to from about 72° C. to about 80° C., such as through use of an oven, for homogeneous and equal temperature distribution throughout its entire volume. Such supernatant liquid may then be allowed to cool slowly to, for example, from about 45° C. to about 50° C. for from about 30 to about 35 minutes, while being stirred, for example, continuously stirred, at from about 800 rpm to about 900 rpm. Such supernatant liquid may be placed in a container on a stirring hot plate or within a temperature-controlled jacket for stirring, cooling, and subsequent control of temperature so that temperature of such supernatant liquid may remain with a range of from about 45° C. to about 50° C. While such supernatant liquid is still stirring, for example, continuously stirring, an amount of sodium silicate of, for example, from about 0.3% to about 0.5% of dry weight of active substance may be added to such a stirring supernatant liquid to form a stable silica-organic complex to impart a gelatinous consistency to a resulting product; such a mixture may be stirred for, for example, from about 5 to about 7 minutes. About 0.08% (this percentage being the ratio of (a) the weight of sodium carbonate to be added to (b) the weight of the substance to which the sodium carbonate is to be added) of sodium carbonate may then be added, and such a mixture may be stirred for, for example, from about 1 to about 2 minutes to enhance mixture with carbonates; which may be followed by a trace amount of dissolved calcium conversion to colloidal sizes insoluble calcium carbonates, which begins humic acid polymerization.

To begin such a polymerization process, approximately 4 to 8 of drops of sulfuric acid may be added in order to lower the pH of the liquid to which such sulfuric acid is added, catalyzing such a process. Hydrochloric acid, for example, 23N solution (as 36% HCl), may then be slowly added in portions to lower the pH to from about 7.0 to about 7.4, for example, to pH 7.2. Each portion of HCl added may be equivalent to from about 0.1% to about 0.2% of total volume to avoid coagulation of humic acids at local sites and formation of small lumps; such liquid mixture may be homogeneously mixed following such addition of each small portion of hydrochloric acid. Protons, i.e. positively charged ions of hydrogen, may replace respectively potassium and/or sodium cations in humic acid molecules, which results in lowering their negative charge and interaction with molecules, resulting in long volumetric chains biopolymer formation. In some embodiments hydrochloric acid may be concentrated, and in other embodiments hydrochloric acid may be diluted. Following each mixing session, any foam resulting from such a reaction may be skimmed from the top of the mixture. After, for example, from about 2.9% to about 3.2% hydrochloric acid has been added, the pH may be checked to determine whether pH of the mixture is from about 7.0 to about 7.4, such as about pH 7.2. A pH below 7 may result in humic substances coagulating with each other, thus resulting in a loss or reduction of biological activity of such humic substances. Such a range of pH allows chemical process stabilization within some period of time, reaching a target pH of, for example, from about 7.5 to about 8.0. A higher original pH may result in a higher final pH, which may cause irritation of skin as well as reduction of biological activity. Irritation may appear at pH above 9. Additionally, the temperature may be checked to determine whether the temperature of such a liquid mixture is, for example, from about 45° C. to about 50° C. Such a polymerization process may turn dissolved humic acids into long biopolymer chains, with part of them in a dissolved state, being polyelectrolyte, resulting in biologically active polyelectrolyte enhanced biopolymer with desired physical properties, such as viscosity, thickness, stickiness and solubility that are convenient for practical application as skin topical cream or gel.

In some embodiments, a commercially available preservative package, comprising from about 0.5% to about 1% of total volume of such a polyelectrolyte enhanced biopolymer mixture, may be added, for example, slowly and uniformly added, to such a mixture. Such a resulting mixture may then be stirred for, for example, about 5 minutes to ensure an even distribution. In some embodiments, such a commercially available preservative package may be Geogard™ ECT, a package designed for use in personal care products. Geogard™ ECT contains benzyl alcohol, salicylic acid, glycerin, and sorbic acid, which provide broad spectrum protection against Gram-positive bacteria, Gram-negative bacteria, yeast, and molds. In some embodiments, any of various additional commercially available preservative packages may be added. In some embodiments, any of various proprietary preservative mixtures may be added. In some embodiments, such a polyelectrolyte enhanced biopolymer mixture may undergo a step of pasteurization in order to slow growth of microbial organisms. During such a pasteurization step such a liquid mixture may be heated to, for example, from about 80° C. to about 95° C., for, for example, about 1 hour. A temperature above 95° C. may result in humic acid molecule functional group inactivation and loss or diminution of their biological activity. Such pasteurization may be undertaken, for example, in place of addition a commercially available or proprietary preservative mixture. Sterilization at a high temperature, for example, at 137° C. and higher, may also be acceptable, but for a limited period of time, for example, for less than one hour, to avoid humic acid molecule functional group inactivation.

A polymerization process may begin when the temperature of a liquid mixture such as is described above is between, for example, from about 72° C. to about 80° C., and may finish as such a liquid mixture cools to a temperature of, for example, from about 45° C. to about 50° C. A temperature of about 45° C. may be above such a mixture's melting temperature, allowing such a mixture to remain in a liquid form. A temperature of about 50° C. or less may allow a commercially available preservative package, or a proprietary preservative mixture, to be added to such a liquid without thermal decomposition or loss of preservative properties. A final viscosity of such a liquid at such an indicated temperature range may be such that it can flow through, for example, about a 1.5 mm sieve, which may be, for example, a final processing step. Passing such a liquid, which contains humic-based polyelectrolyte-enhanced polymer, through such a 1.5 mm sieve also may allow for removal of accumulated foam that may result from such a polymerization reaction and associated stirring. Additionally, such a 1.5 mm sieve may remove any small, soft lumps remaining from coagulation during such a polymerization process. While still at a temperature from about 45° C. to about 50° C., such a liquid may be dispensed into product packaging, as such a product's melting temperature may be, for example, from about 42° C. to about 44° C. As such a liquid substance cools in such packaging, and such substance's temperature drops below such substance's melting temperature, such substance may solidify into a spreadable gel.

Such a resulting product is, for example, a black spreadable gel suitable for topical application to a human body, such a product having a final composition of, for example: about 98.5% polyelectrolyte-enhanced biopolymer made from humic substances derived from brown coal by alkaline extraction and polymerized as a result of addition of sodium carbonate, sulfuric acid and hydrochloric acid; from about 0.3% to about 0.5% of sodium silicate, which may function as solidifying agent and may give such a product a gelatinous consistency; from about 0.38% to about 0.42% benzyl alcohol; from about 0.04% to about 0.07% salicylic acid; from about 0.015% to about 0.025% glycerin; and, from about 0.005% to about 0.02% sorbic acid. A polyelectrolyte-enhanced biopolymer of such disclosed composition comprises concentrated polymerized humic substances extracted from brown coal, such as leonardite or lignite, and converted into biopolymer as a result of addition of sodium carbonate, sulfuric acid and hydrochloric acid additives at an appropriate temperature. In such a composition, benzyl alcohol, salicylic acid, glycerin, and sorbic acid may serve to limit the growth of microbial organisms. A user/consumer may apply such a topical gel at home, as it is water soluble and may be washed down a household drain after use without difficulty.

Many modifications and other embodiments of a process such as is described in various embodiments herein will come to mind to one skilled in the art. Therefore, it is to be understood that a process such as is described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "having," "containing," "involving," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

Any result according to a process such as is described herein is an unexpected result. Any variable that may be inferred as being a result-effective variable according to a process such as is described herein is not recognized in the art to be a result-effective variable.

The foregoing description of methods and embodiments have been presented for purposes of illustration. It is not intended to be exhaustive or to limit the precise steps and/or forms disclosed, and obviously many modifications and variations are possible in light of the above teaching. It is intended that the scope and all equivalents be defined by the claims appended hereto.

What is claimed is:

1. A process for making a composition comprising a biologically active polyelectrolyte enhanced biopolymer, the process comprising:
   (a) contacting an alkaline liquid with a composition comprising humic substances, thereby making a liquid extract enriched in humic substances and a particulate depleted of humic substances;
   (b) adding sodium silicate and sodium carbonate to the liquid extract enriched in humic substances while the liquid extract enriched in humic substances is being stirred continuously and is being cooled from a temperature of from about 72° C. to about 80° C. to a temperature of from about 45° C. to about 50° C., thereby making a salt-treated extract; and
   (c) adding a catalytic amount of one or more acids to the salt-treated extract, the catalytic amount sufficient to catalyze polymerization of humic substances in the salt-treated extract, thereby making the composition comprising the biologically active polyelectrolyte enhanced biopolymer.

2. The process of claim 1, wherein the alkaline liquid is made by adding dry alkali to water or to a mixture of water and the composition comprising humic substances.

3. The process of claim 2, wherein the dry alkali comprises sodium hydroxide, potassium hydroxide or a mixture of sodium hydroxide and potassium hydroxide.

4. The process of claim 1, wherein the alkaline liquid is at a temperature of from about 75° C. to about 85° C. when the contacting takes place.

5. The process of claim 1, wherein the one or more acids comprise(s) sulfuric acid, hydrochloric acid, or a mixture of sulfuric acid and hydrochloric acid.

6. A process for making a pH-balanced product comprising polyelectrolyte enhanced biopolymer suitable for topical application to skin, the process comprising:
   (a) contacting an alkaline liquid with a composition comprising humic substances, thereby making a liquid extract enriched in humic substances and a particulate depleted of humic substances;
   (b) adding one or more salts to the liquid extract enriched in humic substances, thereby making a salt-treated extract;
   (c) adding a catalytic amount of one or more first acids to the salt-treated extract, the catalytic amount sufficient to catalyze polymerization of humic substances in the salt-treated extract, thereby making a composition comprising a polyelectrolyte enhanced biopolymer; and
   (d) adding an amount of one or more second acids to the composition comprising the polyelectrolyte enhanced biopolymer, the amount sufficient to adjust pH of the resulting product to a pH suitable for topical application to skin, thereby making the pH-balanced product comprising polyelectrolyte enhanced biopolymer suitable for topical application to skin, wherein the pH is from about 7.5 to about 8.0.

7. The process of claim 6, wherein the alkaline liquid is made by adding dry alkali to water or to a mixture of water and the composition comprising humic substances.

8. The process of claim 7, wherein the dry alkali comprises sodium hydroxide, potassium hydroxide or a mixture of sodium hydroxide and potassium hydroxide.

9. The process of claim 6, wherein the alkaline liquid is at a temperature of from about 75° C. to about 85° C. when the contacting takes place.

10. The process of claim 6, wherein the one or more salts comprise(s) sodium silicate, sodium carbonate, or a mixture of sodium silicate and sodium carbonate.

11. The process of claim 6, wherein the one or more first acids comprise(s) sulfuric acid, hydrochloric acid, or a mixture of sulfuric acid and hydrochloric acid.

12. The process of claim 6, wherein the one or more second acids comprise(s) sulfuric acid, hydrochloric acid, or a mixture of sulfuric acid and hydrochloric acid.

13. The process of claim 6, wherein the adding the amount of one or more second acids adjusts pH of the composition comprising the polyelectrolyte enhanced biopolymer to which the one or more second acids is added to a pH of from about 7.0 to about 7.4, after which adjustment the composition comprising the polyelectrolyte enhanced biopolymer stabilizes through further chemical processes, not comprising addition of any further substances, to a pH of from about 7.5 to about 8.0.

14. The process of claim 6, wherein the adding the one or more salts comprises adding sodium silicate and sodium carbonate to the liquid extract enriched in humic substances while the liquid extract enriched in humic substances is being stirred continuously and is being cooled from a temperature of from about 72° C. to about 80° C. to a temperature of from about 45° C. to about 50° C.

15. The process of claim 1, wherein the adding the catalytic amount of one or more acids to the salt-treated extract comprises adding sulfuric acid to the salt-treated extract at a temperature of from about 45° C. to about 50° C.

16. The process of claim 6, wherein the adding the catalytic amount of one or more acids to the salt-treated extract comprises adding sulfuric acid to the salt-treated extract at a temperature of from about 45° C. to about 50° C., and the adding the amount of one or more second acids to the salt-treated extract comprising the polyelectrolyte enhanced biopolymer comprises adding hydrochloric acid to the composition comprising the polyelectrolyte enhanced biopolymer at a temperature of from about 45° C. to about 50° C.

17. A process for making a pH-balanced product comprising a biologically active polyelectrolyte enhanced biopolymer suitable for topical application to skin, the process comprising:

(a) contacting a dry alkali, water, and a composition comprising humic substances, thereby making a liquid extract enriched in humic substances and a particulate depleted of humic substances;
(b) adding one or more salts to the liquid extract enriched in humic substances, thereby making a salt-treated extract;
(c) adding a catalytic amount of one or more first acids to the salt-treated extract, the catalytic amount sufficient to catalyze polymerization of humic substances in the salt-treated extract, thereby making a composition comprising a biologically active polyelectrolyte enhanced biopolymer; and
(d) adding an amount of one or more second acids to the composition comprising the biologically active polyelectrolyte enhanced biopolymer, the amount sufficient to adjust pH of the resulting product to a pH suitable for topical application to skin, wherein the one or more second acids is added to a pH of from about 7.0 to about 7.4, after which adjustment the composition comprising the biologically active polyelectrolyte enhanced biopolymer stabilizes through further chemical processes, not comprising addition of any further substances, to a pH of from about 7.5 to about 8.0, thereby making the pH-balanced product comprising the biologically active polyelectrolyte enhanced biopolymer suitable for topical application to skin.

* * * * *